US009227326B2

(12) United States Patent
Brewer et al.

(10) Patent No.: US 9,227,326 B2
(45) Date of Patent: Jan. 5, 2016

(54) REMOTE CENTER OF MOTION MECHANISM AND METHOD OF USE

(75) Inventors: Reuben D. Brewer, Millbrae, CA (US); J. Kenneth Salisbury, Jr., Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 334 days.

(21) Appl. No.: 13/572,452

(22) Filed: Aug. 10, 2012

(65) Prior Publication Data

US 2013/0039732 A1  Feb. 14, 2013

Related U.S. Application Data

(60) Provisional application No. 61/522,530, filed on Aug. 11, 2011.

(51) Int. Cl.
| | |
|---|---|
| *A61B 17/00* | (2006.01) |
| *B25J 18/00* | (2006.01) |
| *B60R 22/03* | (2006.01) |
| *A61B 19/00* | (2006.01) |
| *A61M 5/00* | (2006.01) |
| *B60R 22/02* | (2006.01) |

(52) U.S. Cl.
CPC ............. *B25J 18/00* (2013.01); *A61B 17/00* (2013.01); *A61B 19/22* (2013.01); *A61M 5/00* (2013.01); *B60R 22/03* (2013.01); *A61B 19/2203* (2013.01); *B60R 2022/021* (2013.01)

(58) Field of Classification Search
CPC .... A61B 17/00; A61B 19/22; A61B 19/2203; A61M 5/00; B25J 18/00

USPC .......................... 74/490.03–490.05; 600/427; 901/15–16, 23; 606/1, 130

See application file for complete search history.

(56) References Cited

U.S. PATENT DOCUMENTS

| | | |
|---|---|---|
| 5,397,323 A | 3/1995 | Taylor et al. |
| 5,515,478 A | 5/1996 | Wang |
| 5,630,431 A | 5/1997 | Taylor |
| 5,817,084 A | 10/1998 | Jensen |
| 5,890,396 A | 4/1999 | Kaneko et al. |
| 5,907,664 A | 5/1999 | Wang et al. |
| 6,047,610 A | 4/2000 | Stocco et al. |
| 6,246,200 B1 | 6/2001 | Blumenkranz et al. |
| 6,645,196 B1 | 11/2003 | Nixon et al. |
| 6,665,554 B1 | 12/2003 | Charles et al. |
| 6,723,106 B1 | 4/2004 | Charles et al. |
| 7,021,173 B2 | 4/2006 | Stoianovici et al. |

(Continued)

FOREIGN PATENT DOCUMENTS

| | | |
|---|---|---|
| JP | H04-13578 | 1/1992 |
| SU | 1303150 A1 | 4/1987 |

(Continued)

*Primary Examiner* — Gary Jackson
*Assistant Examiner* — Scott T Luan
(74) *Attorney, Agent, or Firm* — Shay Glenn LLP

(57) ABSTRACT

According to one exemplary embodiment, a manipulator device includes a base, first and second linear slides, a drive link, a drive member, a driven member and an end effector. The elements of the manipulator device cooperate to constrain the end effector to rotate about a remote center of motion that is displaced from a proximal center of motion as the drive link moves a carriage of the second linear slide along an arcuate path.

18 Claims, 13 Drawing Sheets

(56) References Cited

U.S. PATENT DOCUMENTS

| | | |
|---|---|---|
| 2006/0106345 A1* | 5/2006 | Flaker et al. ................. 604/131 |
| 2008/0262513 A1* | 10/2008 | Stahler et al. ................ 606/130 |
| 2010/0121347 A1 | 5/2010 | Jaspers |
| 2011/0282351 A1 | 11/2011 | Cooper et al. |
| 2012/0152050 A1* | 6/2012 | Richardson ................ 74/490.02 |

FOREIGN PATENT DOCUMENTS

| | | |
|---|---|---|
| WO | WO2010/122563 A1 | 10/2010 |
| WO | WO2010/130817 A1 | 11/2010 |

* cited by examiner

REMOTE CENTER OF MOTION MECHANISM AND METHOD OF USE

CROSS REFERENCE TO RELATED APPLICATIONS

This patent application claims priority to provisional patent application Ser. No. 61/522,530, filed on Aug. 11, 2011 and titled "REMOTE CENTER OF MOTION MECHANISM AND METHOD OF USE."

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to medical devices and, more particularly, to an apparatus for guiding a medical tool.

BACKGROUND

Apparatus for guiding medical tools have been shown to be of valuable assistance in various medical procedures, for example, manipulation of surgical tools, manipulation of cameras or sensors, biopsy, etc. An apparatus for guiding a medical tool usually also improves reproducibility compared to free-hand medical procedures, for example, surgical or biopsy procedures.

These apparatus typically have one or more degrees of freedom and may be manually driven in that the one or more degrees of freedom may be equipped with a brake with motive force being provided by a human practitioner, or may be automated in that at least one degree of freedom is driven by a computer controlled actuator.

A medical tool often needs to be oriented about a point in, on, or in proximity to a patient's body. However, having the main body of an apparatus that supports the tool located too proximal to the patient's body may be disadvantageous, since the supporting apparatus may, for example, interfere with the view of or access to the patient by the practitioner. An apparatus which can orient a tool about a remote fulcrum or remote center of motion can avoid such disadvantages.

The use of an apparatus that orients a tool about a remote center of motion is known in robotics as described, for example, in U.S. Pat. Nos. 5,397,323; 5,515,478; 5,630,431; 5,817,084; 5,907,664; 6,047,610; 6,246,200; and 7,021,173.

U.S. Pat. No. 5,397,323 to Taylor et al. discloses the remote center of motion principle in surgical robots with a first axis of rotation pointing into the remote center of motion, and a second axis materialized by a parallelogram mechanism implemented by two coupled parallel linkages of rigid bars and cylindrical joints. The two axes of the remote center of motion are orthogonal, and the mechanism operated around an upright initial (zero) direction.

Unfortunately, the parallelogram structure of Taylor et al. and other conventional parallelogram mechanisms is bulky, making it difficult to position with respect to a patient's body and in some cases forcing a patient to assume an uncomfortable or unconventional position. Therefore, there is a need for an alternative apparatus for guiding medical tools.

U.S. Pat. No. 5,817,084 discloses another exemplary linkage that provides a remote center of motion. The disclosed linkage arrangement allows the motors for positioning the insertion axis to be at a distance from the center of motion. However, the first motor is required to move the entire mass of the second motor in the disclosed linkage arrangement. This requires a larger first motor. The second motor sweeps out a volume as it is moved. Both of these shortcomings increase the mass and bulk of the disclosed linkage arrangement.

In certain applications it is desirable to provide a robotic manipulator device having an end effector that can pass through a small opening in a wall. One way this can be done is to introduce the end effector along an insertion axis with the axis constrained to rotate about a point substantially at the point where the insertion axis intersects the wall, which may be termed the center of motion for the insertion axis.

It will be appreciated that the position of the end effector can be expressed in a spherical coordinate system with an origin at the center of motion. The end effector position may be expressed as two angular displacements and a radius, which is the distance from the center of motion to the end effector. Thus the end effector can be positioned at any point within the range of motion of the robotic manipulator while passing through a small opening in a wall.

One application of such a robotic manipulator is the positioning of an end effector for performing surgical procedures. Minimally invasive surgery (MIS) provides surgical techniques for operating on a patient through small incisions using a camera and elongate surgical instruments introduced to an internal surgical site, often through trocar sleeves or cannulas. The surgical site often comprises a body cavity, such as the patient's abdomen. The body cavity may optionally be distended using a clear fluid such as an insufflation gas. In robotic minimally invasive surgery, the surgeon manipulates the tissues using end effectors of the elongate surgical instruments by remotely manipulating the instruments while viewing the surgical site on a video monitor. As previously mentioned, it may be impractical to place the motors for positioning the insertion axis in proximity to the center of motion. The robotic manipulator may include linkages to couple the motors for positioning the insertion axis at a distance from the center of motion.

The manipulator devices and methods disclosed herein provide advantages over those of the prior art.

SUMMARY OF THE DISCLOSURE

According to one exemplary embodiment, a manipulator device includes a base, first and second linear slides, a drive link, a drive member, a driven member and an end effector. The first linear slide is mounted to the base and has a first carriage movable along a first axis. The second linear slide is mounted to the first carriage and has a second carriage movable along a second axis orthogonal to the first axis. The drive link is coupled between the base and the second carriage and is rotatable about a proximal center of motion that is fixed relative to the base. The drive link is configured to move the second carriage in a constant radius arcuate path relative to the base. The first and second linear slides constrain the second carriage to have a non-rotating orientation relative to the base as the second carriage moves along the arcuate path. The drive member is carried by the second carriage and is connected to the drive link such that the drive member rotates with respect to the second carriage as it moves along the arcuate path but maintains the same rotational orientation as the drive link. The driven member is also carried by the second carriage. The driven member is laterally spaced apart from and rotationally coupled to the drive member such that the driven member rotates with respect to the second carriage as it moves along the arcuate path but maintains the same rotational orientation as the drive member and the drive link. The end effector is carried by the second carriage and is rotationally coupled to the driven member such that the end effector maintains the same rotational orientation as the driven member, the drive member, and the drive link. The elements of the manipulator device cooperate to constrain the end effector to rotate about a remote center of motion that is displaced from the proximal center of motion as the drive link moves the second carriage along the arcuate path.

In some embodiments, the base is rotatable about an axis that intersects the proximal center of motion and the remote center of motion such that the end effector is spherically rotatable in two degrees of freedom about the remote center of motion.

In some embodiments, the manipulator device comprises a prime mover coupled to the drive link and configured to move the second carriage along the arcuate path. The device may include an automated mode in which at least one degree of freedom is driven by a computer controlled actuator. In some embodiments, the end effector is configured to be manually moved, and the drive link is configured to follow the motion of the second carriage and constrain the second carriage to move along the arcuate path. The manipulator device may include a powered assist mode in which manual movements of the end effector are sensed and a prime mover provides force to assist with those movements. The device may include a manual mode and a powered assist mode as previously described, and an automated mode in which at least one degree of freedom is driven by a computer controlled actuator.

In some embodiments of the manipulator device, the end effector comprises an intravenous line inserter. In some embodiments, the device comprises shaft encoders to provide feedback of rotational positions in the two degrees of freedom about the remote center of motion.

Methods of using the above manipulator devices are also disclosed.

Areas of use for the methods and devices disclosed herein include, for example, laparoscopic surgery, intravenous line insertion, and stapedectomy (ear surgery), each with or without robotic assistance.

Other features and advantages of the present invention will be apparent from the accompanying drawings and from the detailed description that follows below.

BRIEF DESCRIPTION OF THE DRAWINGS

A better understanding of the features and advantages of the present invention will be obtained by reference to the following detailed description that sets forth illustrative embodiments, and the accompanying drawings of which.

DETAILED DESCRIPTION

Figure 1:
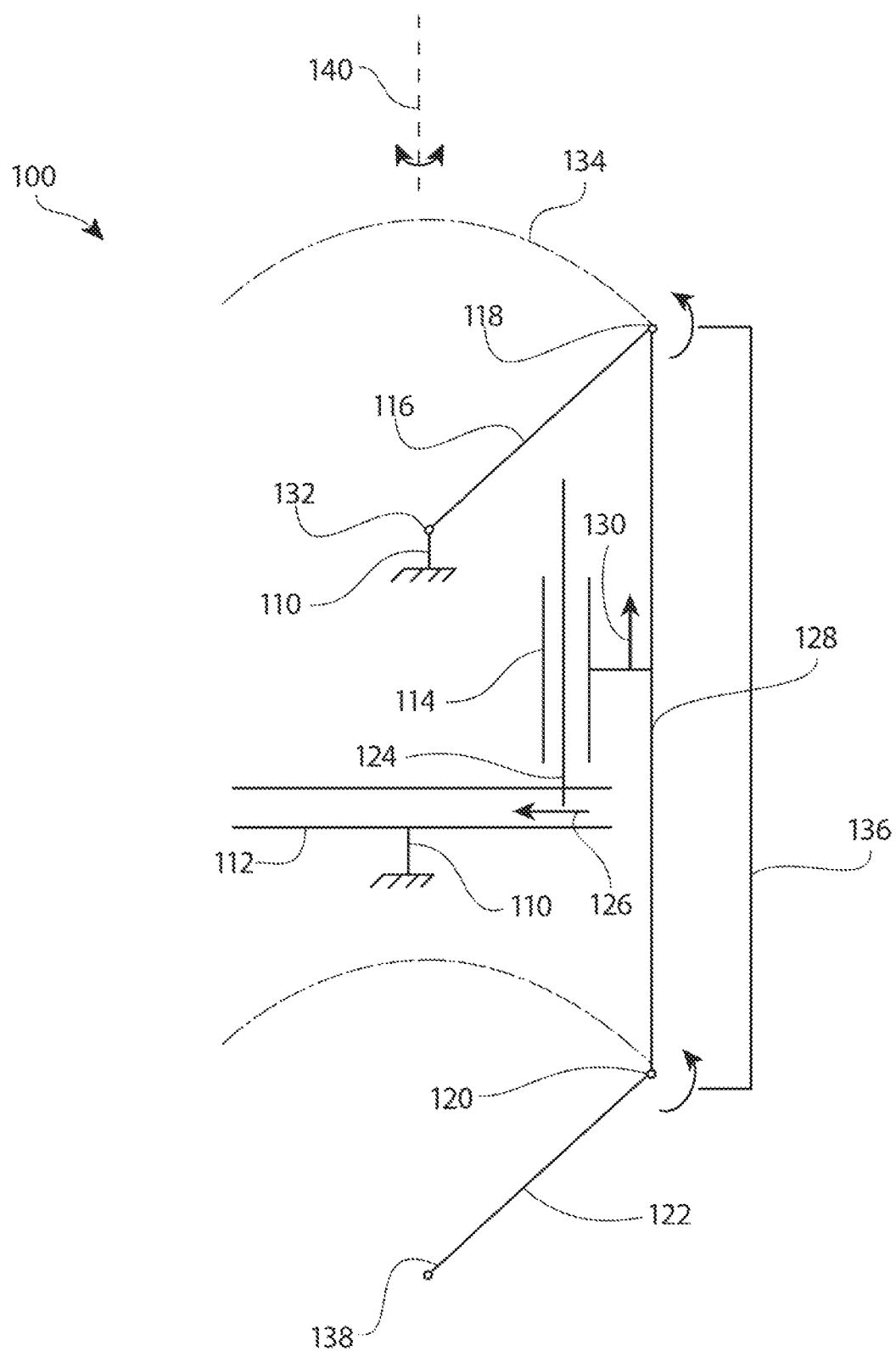
FIG. 1 is a schematic representation of an exemplary remote center of motion device constructed according to aspects of the disclosure.

Referring to FIG. 1, an exemplary manipulator system constructed according to aspects of the disclosure is schematically shown. In this exemplary embodiment, a manipulator device 100 includes a base 110, first and second linear slides 112 and 114, a drive link 116, a drive member 118, a driven member 120 and an end effector 122. The first linear slide 112 is mounted to the base 110 and has a first carriage 124 movable along a first axis 126. The second linear slide 114 is mounted to the first carriage 124 and has a second carriage 128 movable along a second axis 130 orthogonal to the first axis 126. The drive link 116 is coupled between the base 110 and the second carriage 128 and is rotatable about a proximal center of motion 132 that is fixed relative to the base 110. The drive link 116 is configured to move the second carriage 128 in a constant radius arcuate path 134 relative to the base 110. The first and second linear slides 112 and 114 constrain the second carriage 128 to have a non-rotating orientation relative to the base 110 as the second carriage 128 moves along the arcuate path 134. The drive member 118 is carried by the second carriage 128 and is connected to the drive link 116 such that the drive member 118 rotates with respect to the second carriage 128 as it moves along the arcuate path 134 but maintains the same rotational orientation as the drive link 116. The driven member 120 is also carried by the second carriage 128. The driven member 120 is laterally spaced apart from and rotationally coupled to the drive member 118 by a coupling rotational coupling device 136 such that the driven member 120 rotates with respect to the second carriage 128 as it moves along the arcuate path 134 but maintains the same rotational orientation as the drive member 118 and the drive link 116. The end effector 122 is carried by the second carriage 128 and is rotationally coupled to the driven member 120 such that the end effector 122 maintains the same rotational orientation as the driven member 120, the drive member 118, and the drive link 116. The elements of the manipulator device 100 cooperate to constrain the end effector 122 to rotate about a remote center of motion 138 (which may also be referred to as a pitch axis) that is displaced from the proximal center of motion 132 as the drive link 116 moves the second carriage 128 along the arcuate path 134. Thus, in some embodiments, the final desired motion provided by manipulator device 100 is that end effector 122 rotates in a circle, with the tip of end effector 122 always at the center of the circle and the body of end effector 122 always oriented along a radius of the circle.

In some embodiments, the base 110 carrying all of the previously described components is rotatable about a yaw axis 140 that intersects the proximal center of motion axis 132 and the remote center of motion axis 138. With this added degree of freedom, the end effector 122 becomes spherically rotatable in two degrees of freedom about the remote center of motion 138. Thus, in some embodiments, the final desired motion provided by manipulator device 100 is that end effector 122 rotates within a sphere, with the tip of end effector 122 always at the center of the sphere and the body of end effector 122 always oriented along a radius of the sphere.

In some embodiments, the manipulator device 100 further comprises a prime mover (not shown in FIG. 1) coupled to the drive link 116 and configured to move the second carriage 128 along the arcuate path 134. In some embodiments, the end effector 122 of the manipulator device 100 is configured to be manually moved, and the drive link 116 is configured to follow the motion of the second carriage 128. In other words, the drive link 116 and drive member 118 do not actually "drive" the second carriage 128 and the driven member 120, but serve merely to constrain the second carriage 128 to move along the arcuate path 134 and maintain a desired orientation of the end effector 122. In some embodiments, the manipulator device has both an automatically driven mode and a manually operated mode. In some embodiments, the manipulator device has a powered assist mode, in which manual movements of the end effector 122 are sensed and a prime mover provides force to assist with those movements, such as assisting with acceleration, deceleration, and/or maintaining a sensed velocity and/or position. Shaft encoders may be provided as shown to provide feedback of the rotational positions of the pitch and yaw axes.

Figure 3:
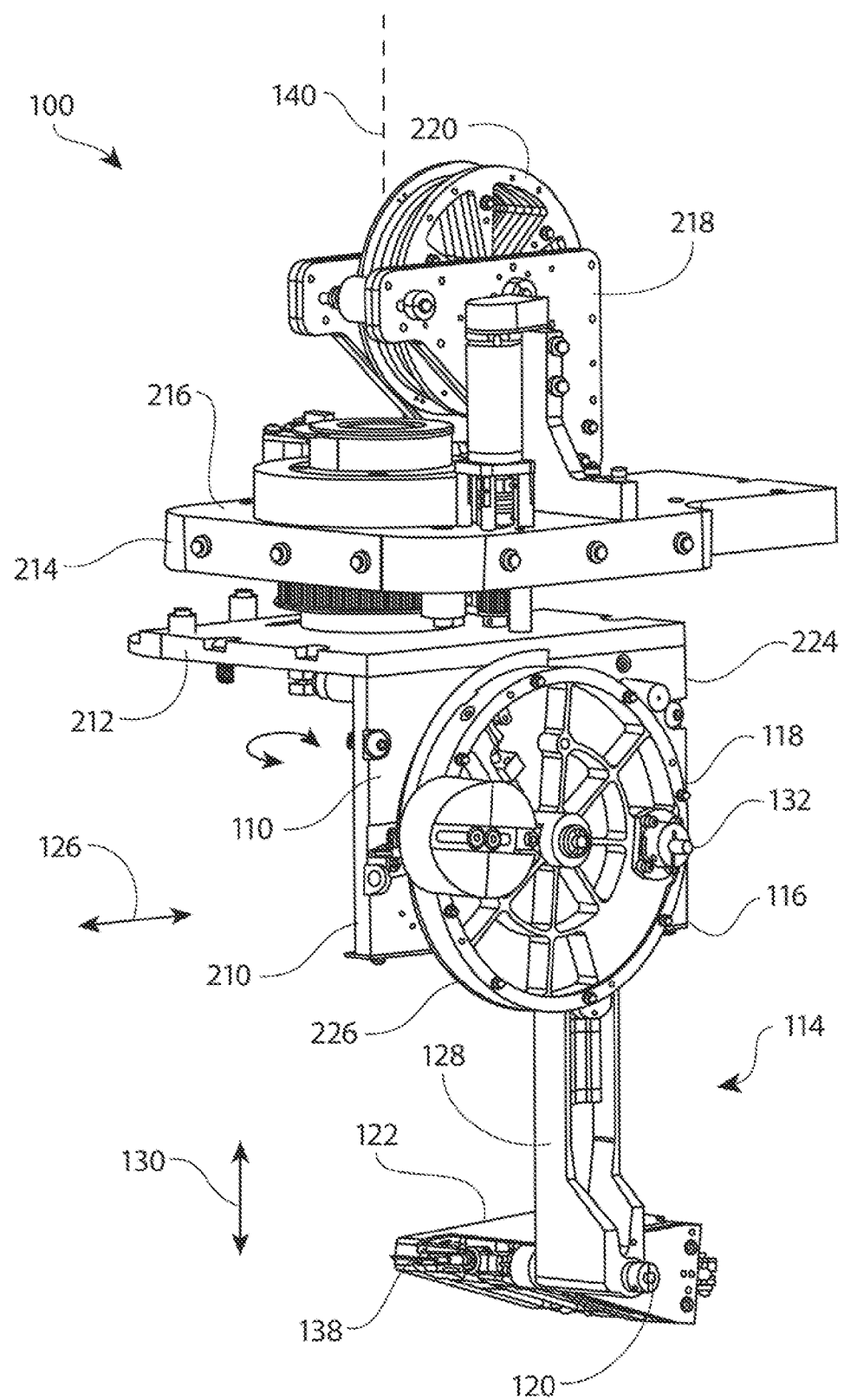
Figure 4:
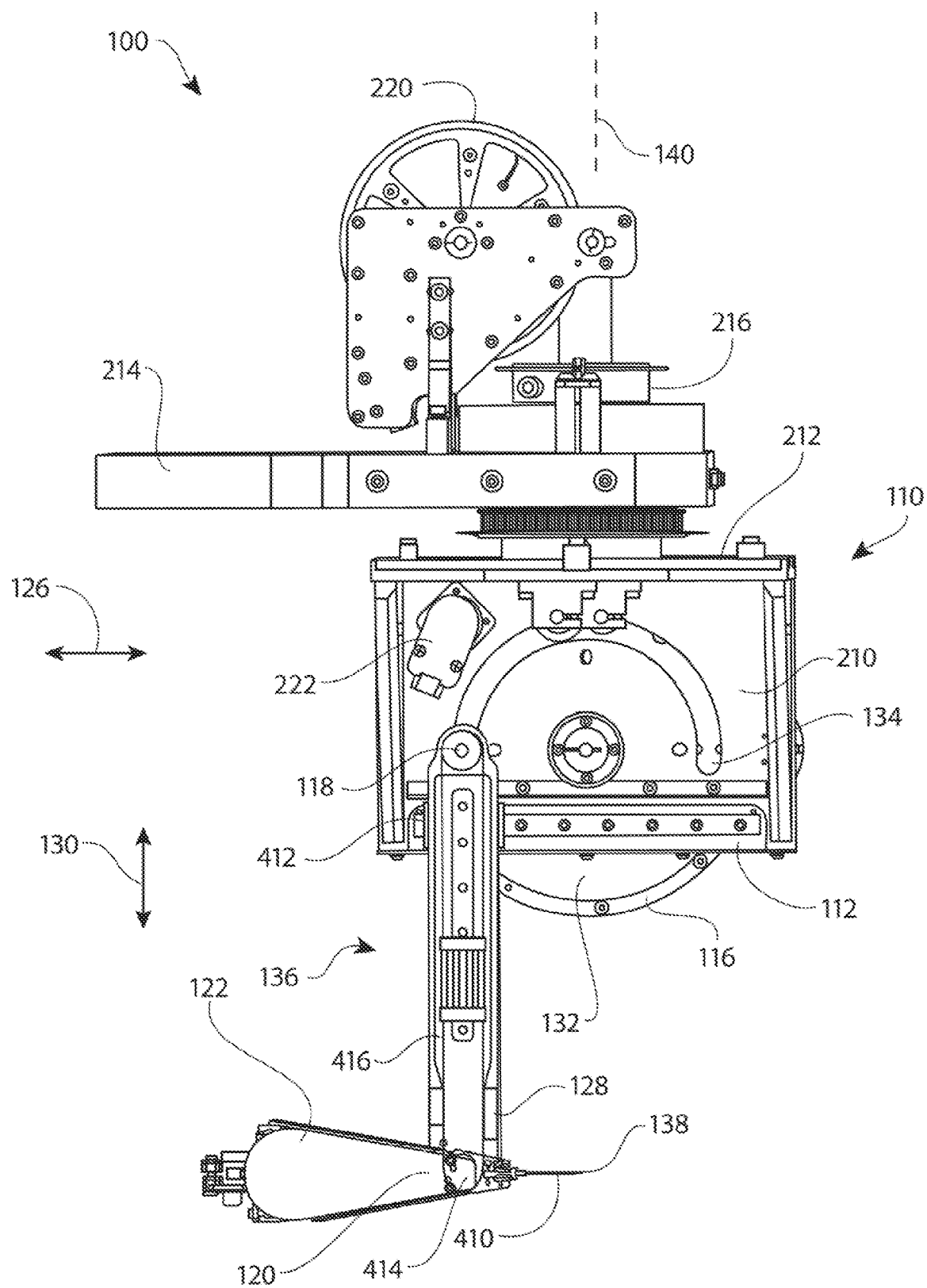
FIGS. 4-6 are a series of front elevation views showing the device of FIG. 1 in a progression of positions.

Referring to FIGS. 3 and 4, further details of exemplary manipulator device 100 are shown. In this exemplary embodiment, base 110 comprises a vertical plate 210 and a horizontal plate 212 attached together in an L-shaped arrangement. Base 110 is rotatably mounted to frame 214 with bearing 216 such that base 110 may be rotated relative to frame 214 about vertical yaw axis 140. A motor 218 may be attached to frame 214 for rotating base 110 through a timing belt pulley and belt system as shown. Frame 214 may be fixed relative to ground, or may add further degrees of freedom by being movably mounted, such as by being vertically adjustable. A constant tension cable spool 220 may be provided atop frame 214 for taking up slack in wires, cables, tubing, etc. (not shown), which may pass from spool 220 through a central aperture in bearing 216 along vertical yaw axis 140 to the pivoting end effector 122.

Figure 7:
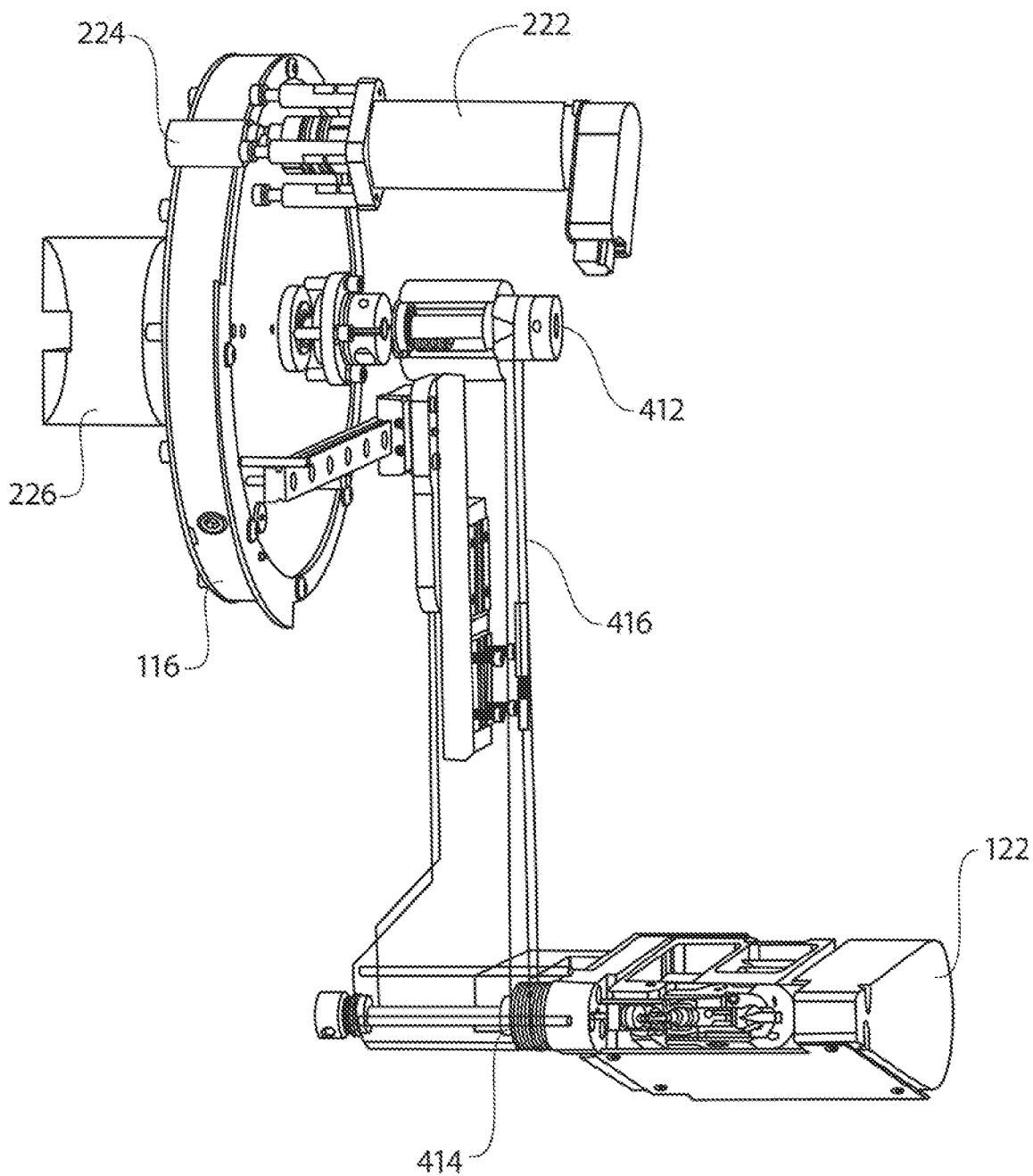
FIG. 7 is a side elevation view showing a lower portion of the device of FIG. 1.
Figure 8:
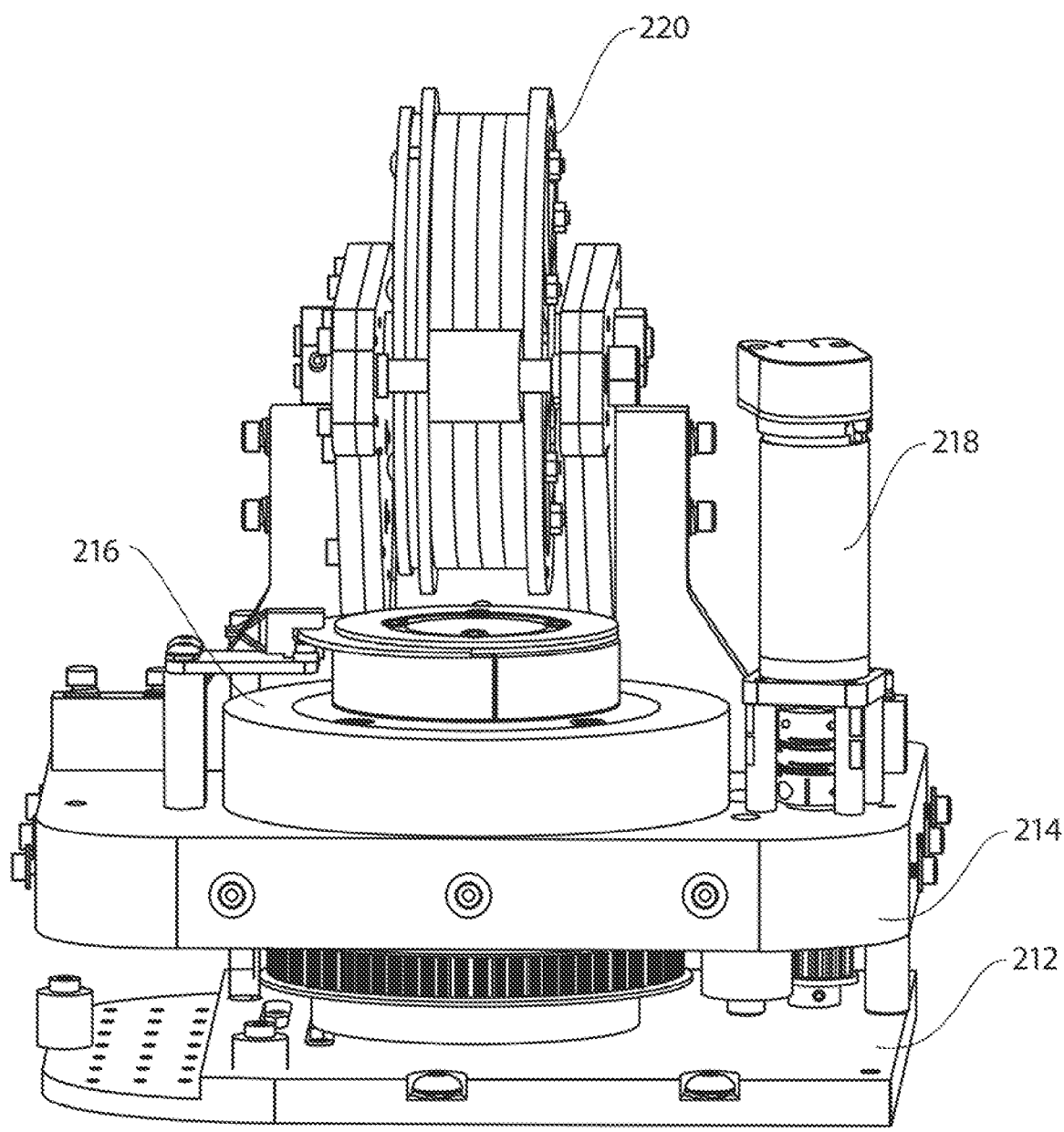
FIG. 8 is a perspective view showing an upper portion of the device of FIG. 1.
Figure 9:
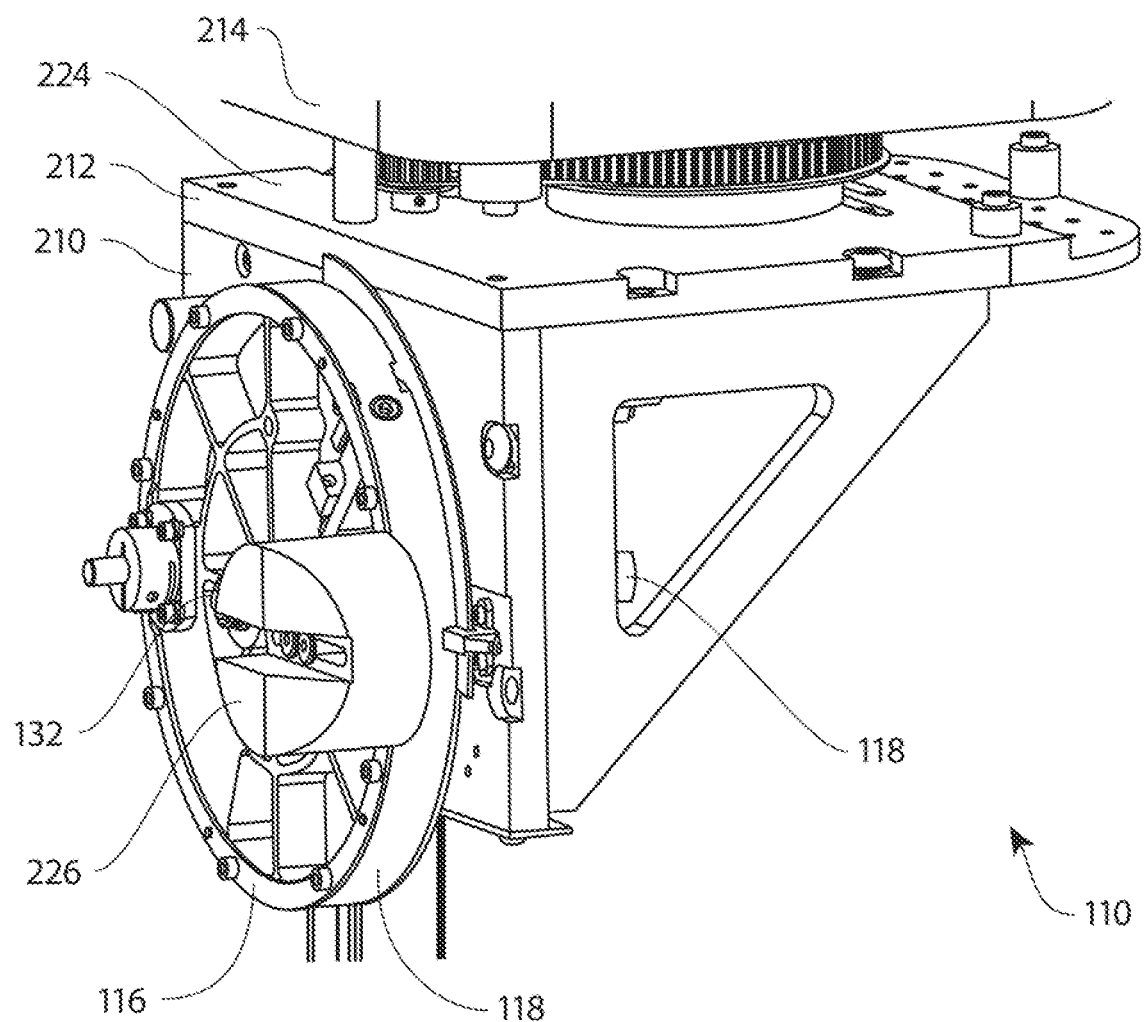
FIG. 9 is an oblique side elevation view showing a rear portion of the device of FIG. 1.
Figure 10:
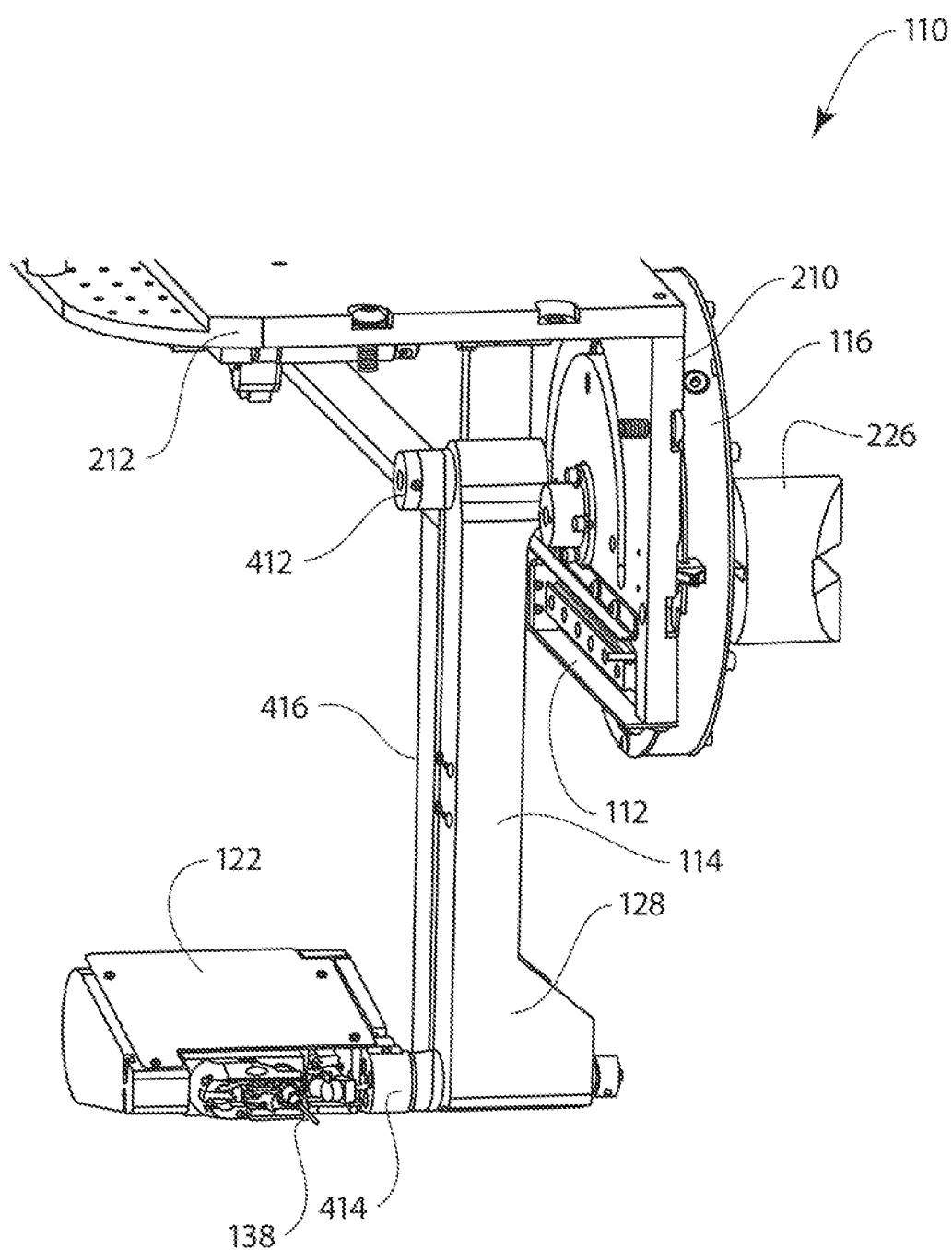
FIG. 10 is an oblique side elevation view showing a front portion of the device of FIG. 1.
Figure 11:
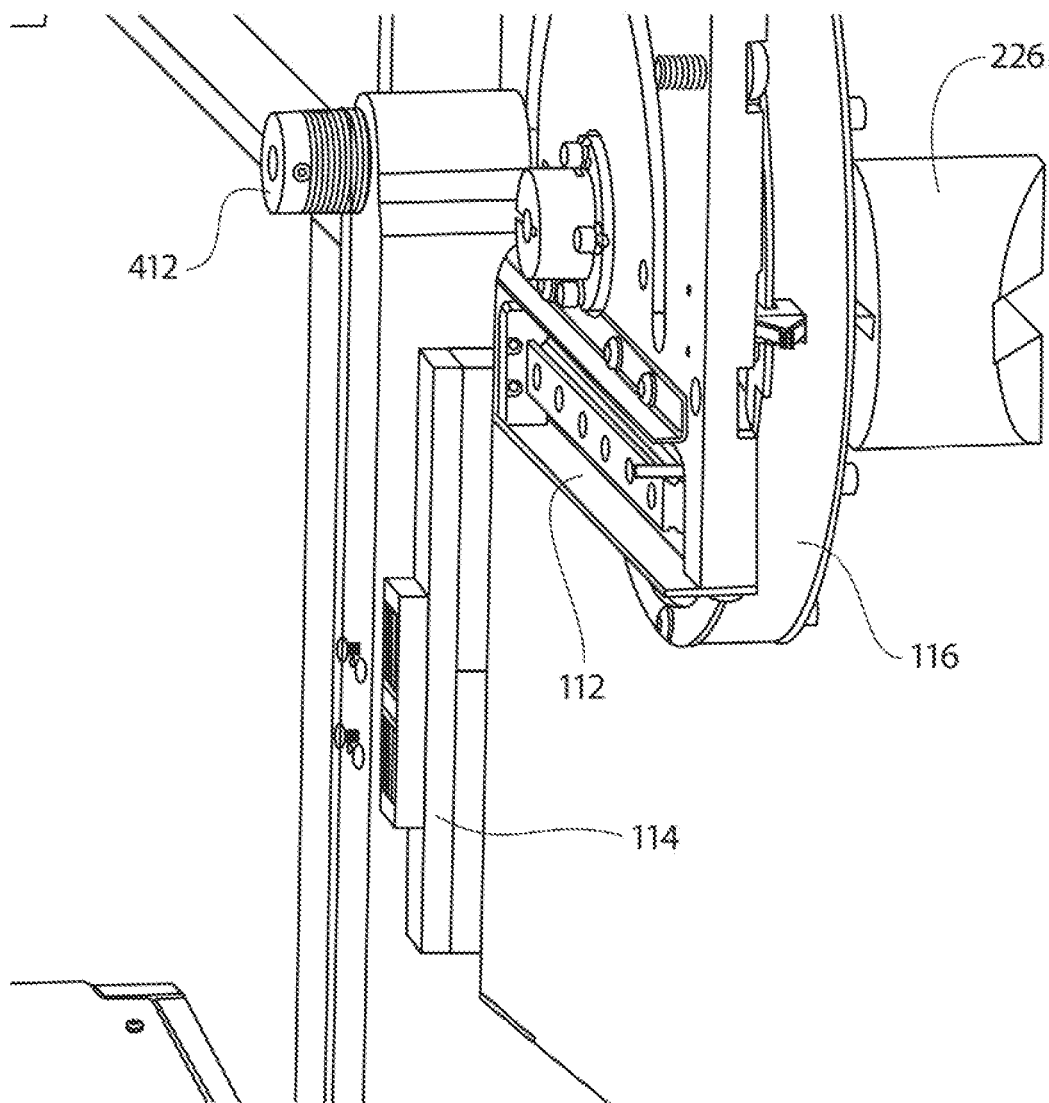
FIG. 11 is an enlarged view showing a portion of FIG. 10.

In this exemplary embodiment, drive link 116 is formed by a wheel mounted with bearings to rotate about the proximal center of motion axis 132. A motor 222 (shown in FIG. 2) may be provided on a front side of base plate 210 for rotatably driving drive link 116 with a capstan 224 (shown in FIGS. 3 and 7) provided on a backside of base plate 210. Capstan 224 drives the outer circumference of drive link wheel 116 to rotate it, such as with a cable transmission having a cable that is wound around capstan 224 and wheel 116.

Figure 2:
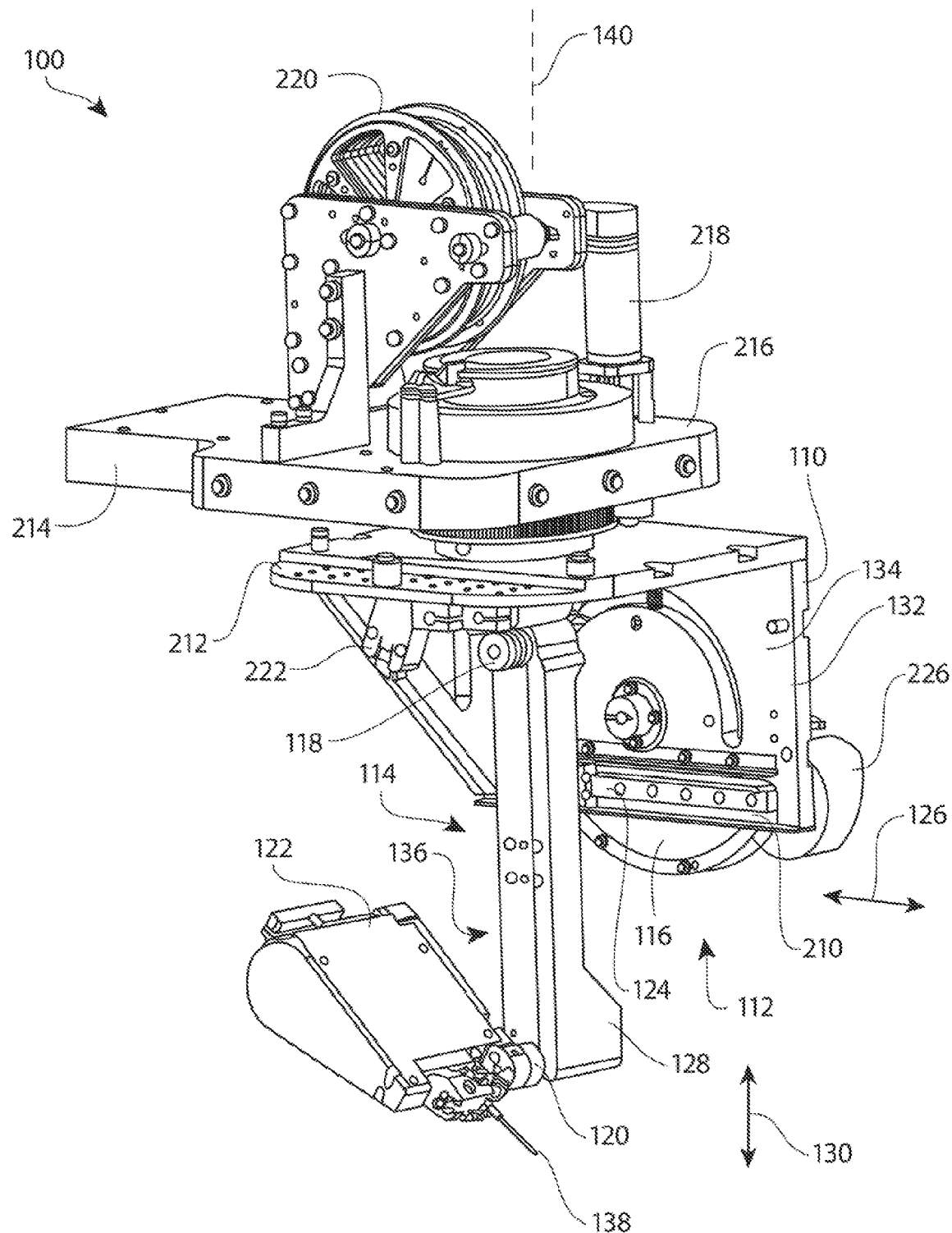
FIGS. 2 and 3 are perspective views showing further details of the device of FIG. 1.

As best seen in FIG. 3, drive member 118 may comprise a shaft rigidly mounted to drive link wheel 116. As best seen in FIG. 2, drive member 118 passes through a slot in base plate 210 which forms arcuate path 134. In this embodiment, drive member 118 may travel about 190 degrees along arcuate path 134. In other embodiments, different ranges of motion may be provided, such as about 45, 90, 180, 270, 350, 360, 450 degrees, or infinite travel. For embodiments having travel greater than about 350 degrees, drive link/wheel 116 or a portion thereof may be mounted on the same side of vertical base plate 210 as slides 112 and 114 so that drive member 118 need not pass through a slot 134 in plate 210. The distal end of drive member 118 may pass through second carriage 128 as shown and may include a cable pulley mounted thereon, as will subsequently be described in further detail. Referring again to FIG. 3, drive link wheel 116 may be provided with a weight 226 opposite from drive member 118 to counterbalance the weight of second slide 114 and end effector 122.

Referring again to FIG. 2, it can be seen that first slide 112 is rigidly mounted to base plate 210, allowing first carriage 124 to travel back and forth horizontally with respect to base plate 210. Second slide 114 is rigidly mounted to first carriage 124, allowing second carriage 128 to travel back and forth vertically with respect to first carriage 124. With this arrangement, driving drive link wheel 116 with motor 222 causes second carriage 128 to travel along arcuate path 134. During this travel, the vertical orientation of second carriage 128 is maintained by virtue of its coupling to base plate 210 through first and second linear slides 112 and 114.

Figure 5:
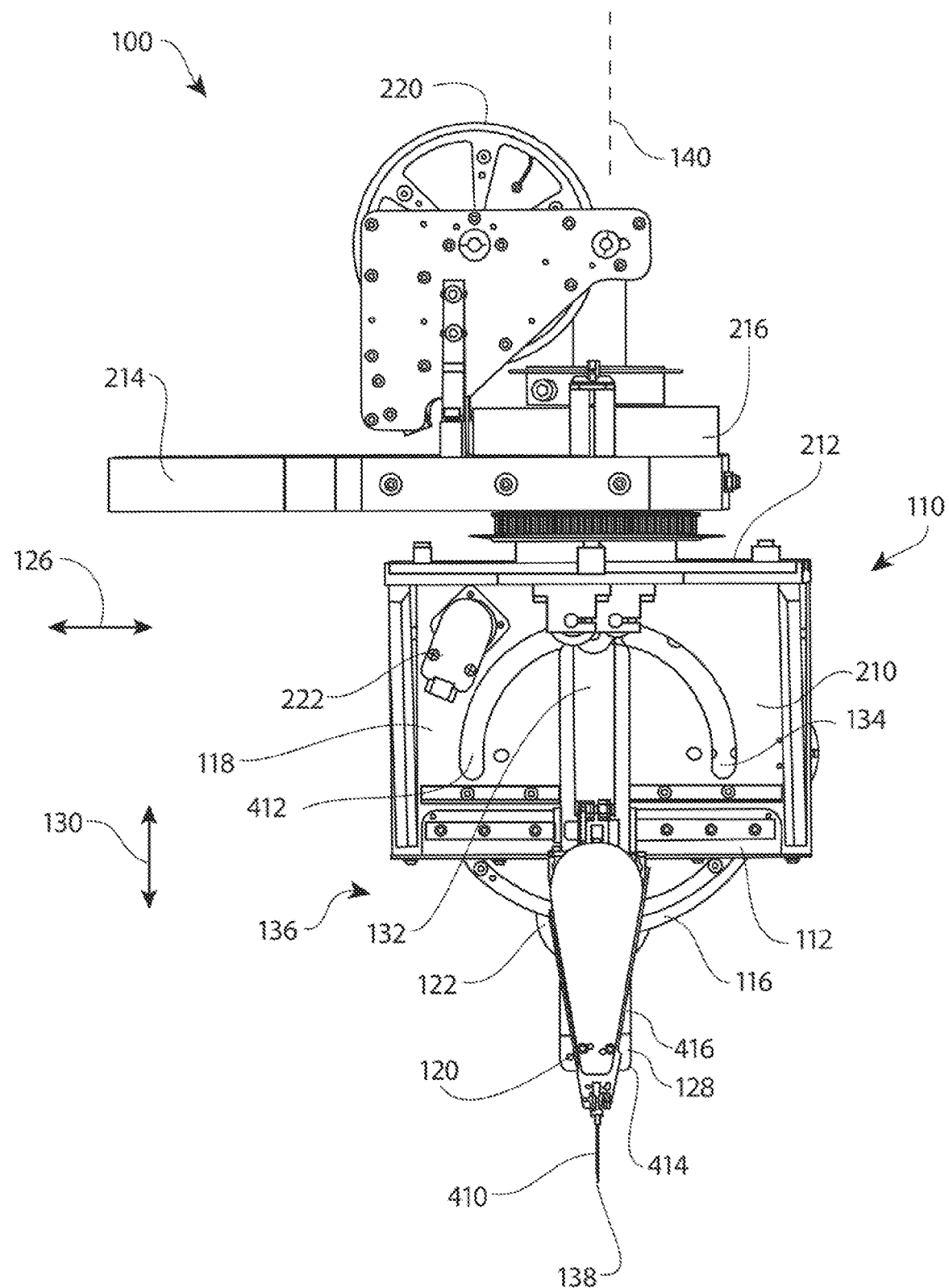
Figure 6:
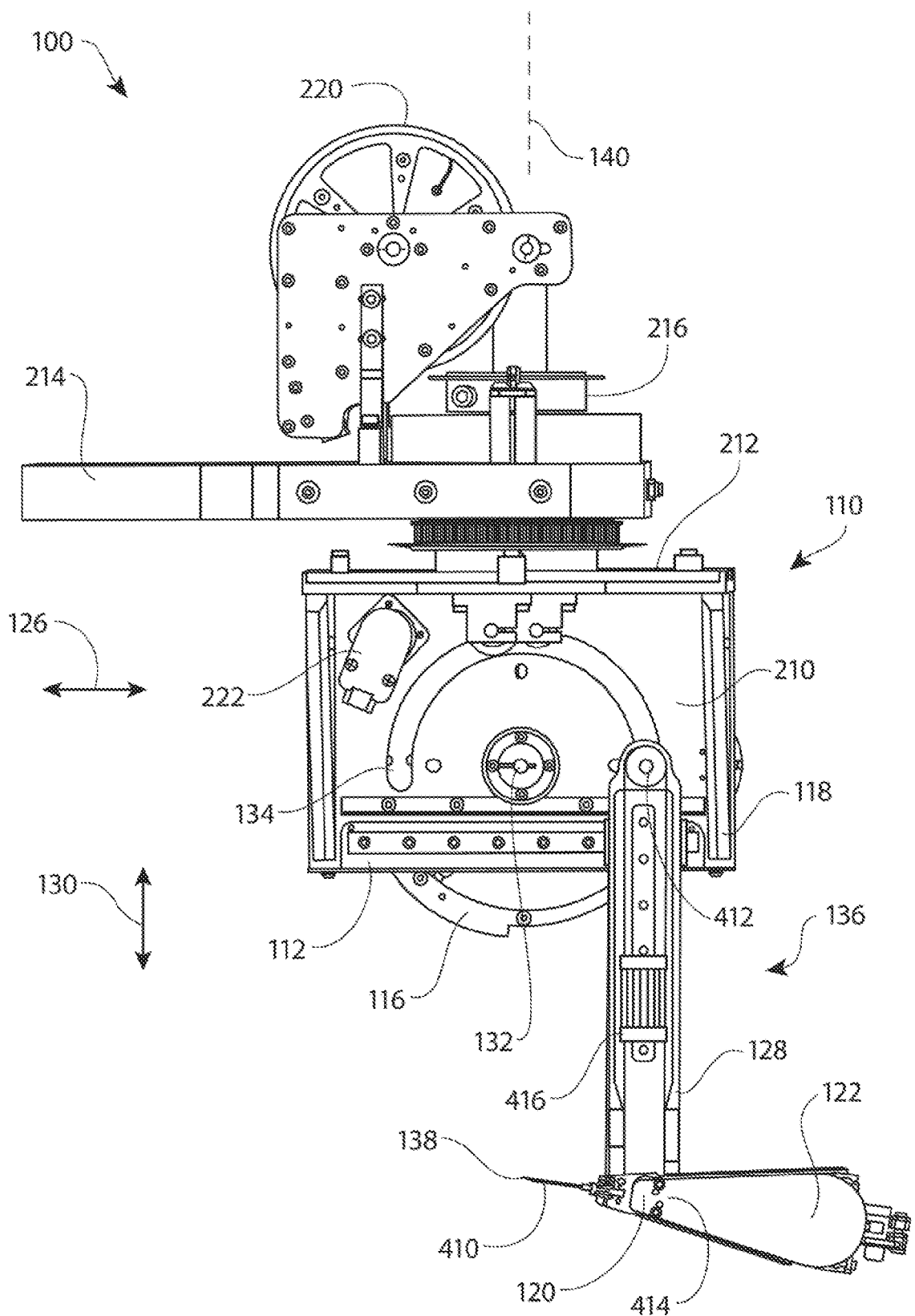

Referring to FIGS. 4-6, the rotation of end effector 122 about the remote center of motion 138 will now be described. It can be seen from the progression of FIGS. 4-6 that as second carriage 128 and end effector 122 travel together along arcuate path 134 from roughly the 9 o'clock position (FIG. 4), through the 12 o'clock position (FIG. 5) to roughly the 3 o'clock position (FIG. 6), end effector 122 changes orientation from pointing roughly 90 degrees to the right (FIG. 4), to pointing straight down (FIG. 5), to pointing roughly 90 degrees to the left (FIG. 6). In this exemplary embodiment, end effector 122 may be an intravenous line inserter. If needle 410 of end effector 122 is arranged so that its distal tip is spaced apart from the axis of rotation of driven member 120 by a distance equal to the spacing between the axis of rotation of drive member 118 and the proximal center of motion 132, the distal tip of needle 410 will always be on the remote center of motion 138 regardless of its pivoting orientation, and the orientation of needle 410 will always be along a radius of a circle having its center on the remote center of motion 138.

Figure 12:
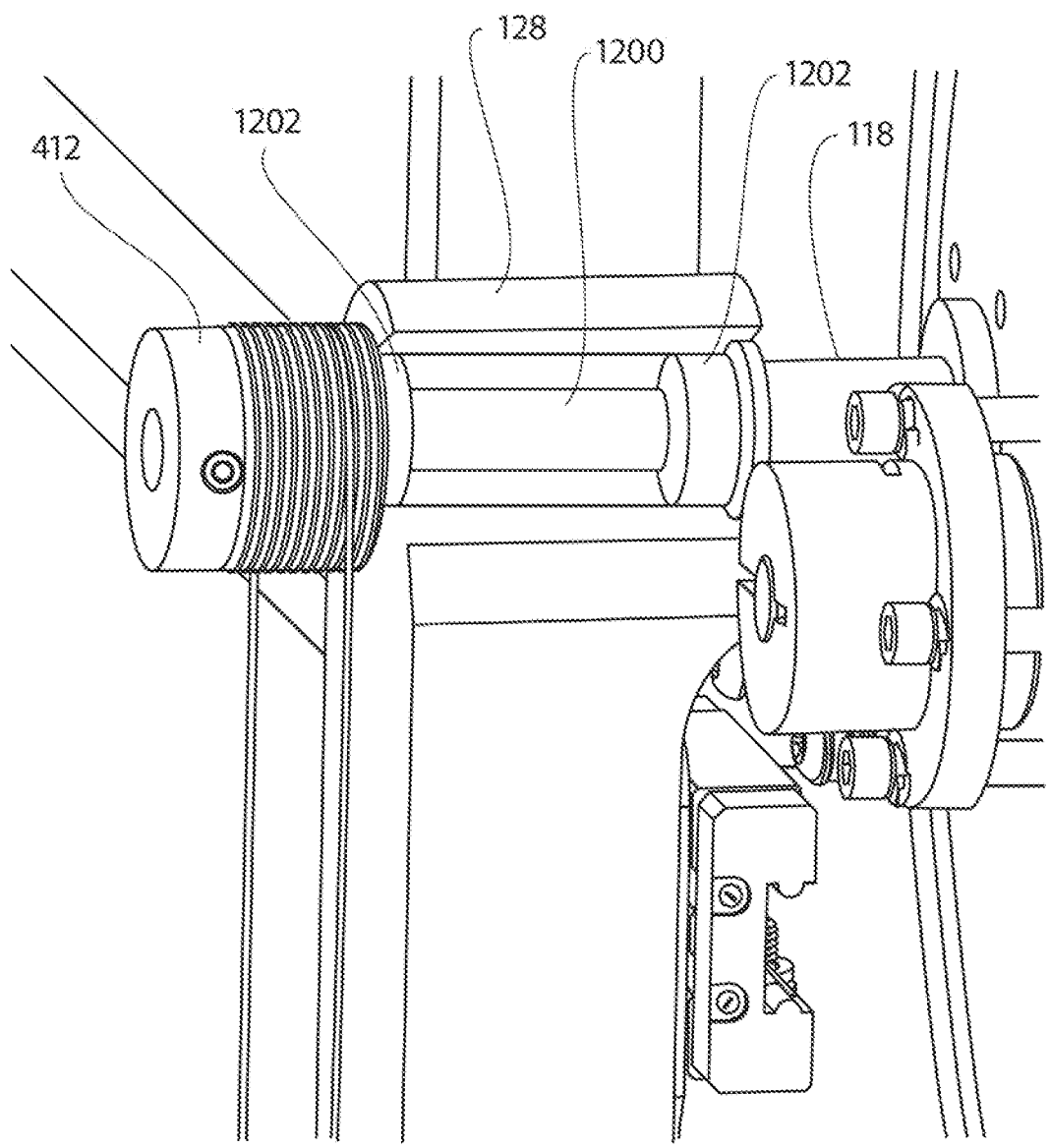
FIG. 12 is a further enlarged view showing a portion of FIG. 11.
Figure 13:
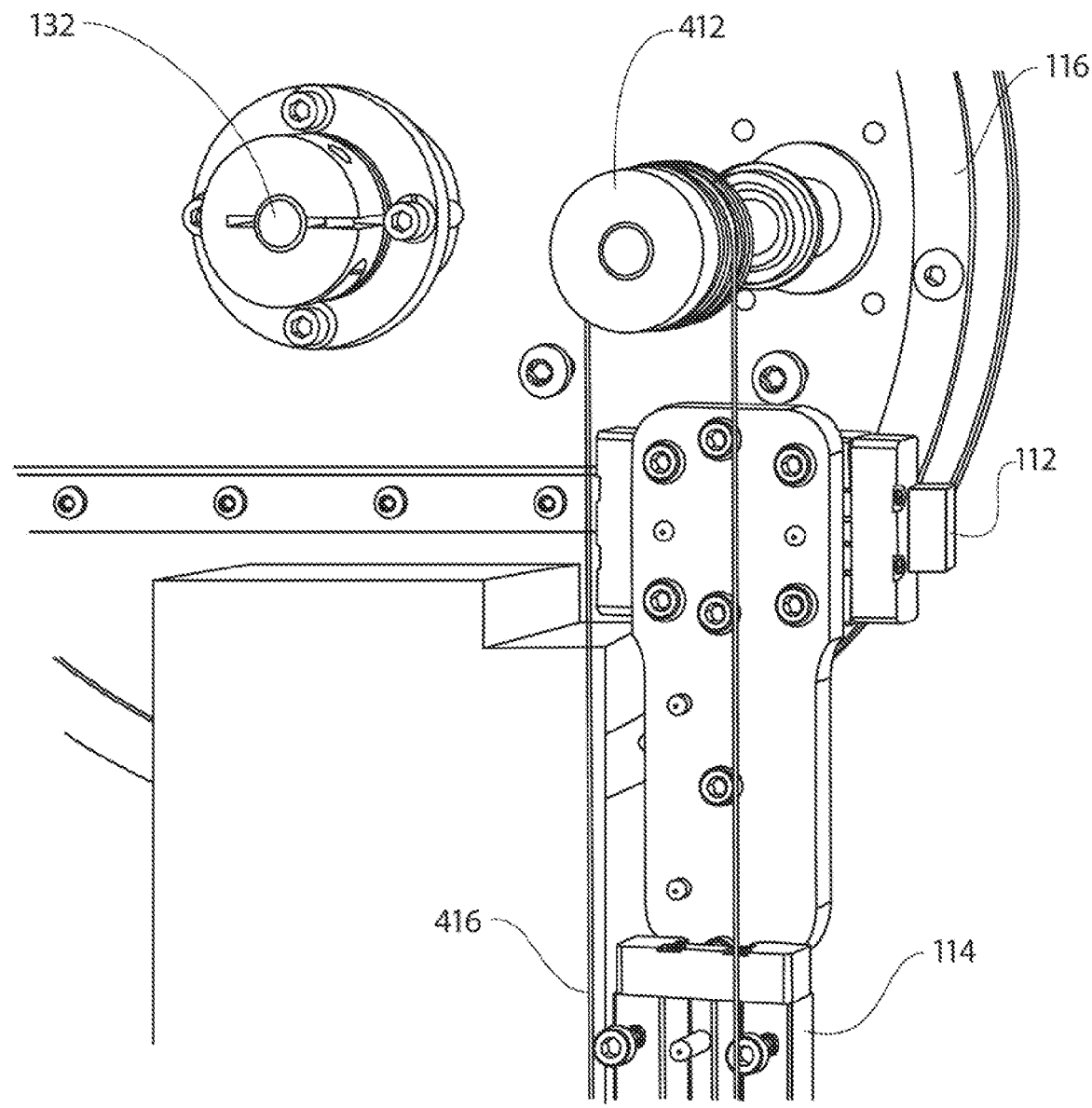
FIG. 13 is an enlarged frontal view showing a calibration tool being used with the exemplary device of FIG. 1.

The above-described pivoting of needle 410 about the remote center of motion 138 is accomplished by rotational coupling device 136, which may include a first pulley 412 rigidly attached to the distal end of drive member 118, a second pulley 414 rigidly attached to the distal end of driven member 120, and a drive cable 416 interconnecting the first and second pulleys. Drive member 118 and driven member 120 may each comprise a shaft 1200 rotatably supported by second carriage 128, such as with bushings or with ball bearings 1202, as best seen in FIG. 12. With this arrangement, first pulley 412 and second pulley 414 rotate in unison relative to second carriage 128. Since drive member 118 is rigidly connected to drive link wheel 116, it can be appreciated that the orientation of first pulley 412 will rotate 180 degrees clockwise as it travels along arcuate path 134 from the 9 o'clock position shown in FIG. 4 to the 3 o'clock position in FIG. 6. During this motion, second pulley 414 will also rotate 180 degrees clockwise since it is rotationally coupled to first pulley 412 by cable 416. Second pulley 414 in turn rotates end effector 122 the same amount.

Further details of exemplary manipulator device 100 are shown in FIGS. 7-13. According to aspects of the disclosure, manipulator device 100 is configured to pass through a vertical inflection point, as depicted in FIGS. 4-6. Device 100 is easy to calibrate, is more compact, and includes fewer moving parts, cables and potential pinch points than prior art remote center of motion manipulators.

As with many robotic manipulators that support and position an end effector with a remote center of motion, manipulator 100 comprises a cantilevered structure. As previously described, manipulator 100 is supported from an end of the structure opposite the end that supports the end effector. In some embodiments it is desirable that the manipulator be stiff so that the position of the end effector can be controlled with great precision. Stiffness may generally be achieved by providing a structure with a high resonant frequency and a low moment of inertia. Thus it is often desirable to minimize the mass of the manipulator and the distance of the mass from the supported end of the cantilevered structure. The arrangement of manipulator 100 advantageously places the motors and other components having a large mass in a compact configuration that minimizes the contribution of these relatively heavy components to the moment of inertia of the manipulator.

In this or other embodiments, either side of a linear slide can be considered a "carriage". In some embodiments, a drive member and a driven member can be a pair of pulleys, sprockets, capstans, gears, lever arms or servos, coupled by one or more cables, chains, belts, gear trains, tie rods, or conductors. Other suitable mechanisms may also be used to transfer rotational orientation between a drive member and a driven member. In some embodiments, a drive link may be a wheel, lever arm, cam groove or other suitable mechanism. A drive link and/or base can be rotated manually, or by one or more prime movers such as an electric motor. The electric motor(s) can be directly controlled by an operator, such as with a hand or foot-operated switch, or may be computer controlled with software.

While exemplary embodiments constructed according to aspects of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A manipulator device comprising:
   a base;
   a first linear slide mounted to the base, the first linear slide having a first carriage movable along a first axis;
   a second linear slide mounted to the first carriage, the second linear slide having a second carriage movable along a second axis orthogonal to the first axis;
   a drive link coupled between the base and the second carriage, the drive link being rotatable about a proximal center of motion that is fixed relative to the base, the drive link being configured to move the second carriage in an arcuate path relative to the base, the arcuate path having a constant radius, wherein the first and the second linear slides constrain the second carriage to have a non-rotating orientation relative to the base as the second carriage moves along the arcuate path;
   a drive member carried by the second carriage and connected to the drive link such that the drive member rotates with respect to the second carriage as it moves along the arcuate path but maintains the same rotational orientation as the drive link;
   a driven member carried by the second carriage, the driven member being laterally spaced apart from and rotationally coupled to the drive member such that the driven member rotates with respect to the second carriage as it moves along the arcuate path but the driven member maintains the same rotational orientation as the drive member and the drive link; and
   an end effector carried by the second carriage and rotationally coupled to the driven member such that the end effector maintains the same rotational orientation as the driven member, the drive member, and the drive link,
   the elements of the manipulator device thereby cooperating to constrain the end effector to rotate about a remote center of motion that is displaced from the proximal center of motion as the drive link moves the second carriage along the arcuate path.

2. The manipulator device of claim 1, wherein the base is rotatable about an axis that intersects the proximal center of motion and the remote center of motion such that the end effector is spherically rotatable in two degrees of freedom about the remote center of motion.

3. The manipulator device of claim 2, wherein the device further comprises shaft encoders to provide feedback of rotational positions in the two degrees of freedom about the remote center of motion.

4. The manipulator device of claim 1, further comprising a prime mover coupled to the drive link and configured to move the second carriage along the arcuate path.

5. The manipulator device of claim 4, wherein the device includes an automated mode in which at least one degree of freedom is driven by a computer controlled actuator.

6. The manipulator device of claim 1, wherein the end effector is configured to be manually moved, and the drive link is configured to follow the motion of the second carriage and constrain the second carriage to move along the arcuate path.

7. The manipulator device of claim 6, wherein the device includes a powered assist mode in which manual movements of the end effector are sensed and a prime mover provides force to assist with those movements.

8. The manipulator device of claim 7, wherein the device includes the manual mode, the powered assist mode, and an automated mode in which at least one degree of freedom is driven by a computer controlled actuator.

9. The manipulator device of claim 1, wherein the end effector comprises an intravenous line inserter.

10. A method of constraining an end effector to rotate about a remote center of motion that is displaced from a proximal center of motion that is fixed relative to a base, the method comprising:
    providing the base and a first linear slide mounted to the base, the first linear slide having a first carriage;
    moving the first carriage along a first axis;
    providing a second linear slide mounted to the first carriage, the second linear slide having a second carriage;
    moving the second carriage along a second axis orthogonal to the first axis;
    providing a drive link coupled between the base and the second carriage;
    rotating the drive link about the proximal center of motion such that the drive link moves the second carriage in an arcuate path relative to the base, the arcuate path having a constant radius, wherein the first and the second linear slides constrain the second carriage to have a non-rotating orientation relative to the base as the second carriage moves along the arcuate path;
    providing a drive member carried by the second carriage and connected to the drive link;
    rotating the drive member with respect to the second carriage as it moves along the arcuate path and maintaining the same rotational orientation as the drive link;
    providing a driven member carried by the second carriage, the driven member being laterally spaced apart from and rotationally coupled to the drive member;
    rotating the driven member with respect to the second carriage as it moves along the arcuate path and maintaining the driven member in the same rotational orientation as the drive member and the drive link; and
    providing an end effector carried by the second carriage and rotationally coupled to the driven member such that the end effector maintains the same rotational orientation as the driven member, the drive member, and the drive link.

11. The method of claim 10, further comprising rotating the base about an axis that intersects the proximal center of motion and the remote center of motion such that the end effector is spherically rotated in two degrees of freedom about the remote center of motion.

12. The method of claim 11, further comprising providing feedback with shaft encoders of rotational positions in the two degrees of freedom about the remote center of motion.

13. The method of claim 10, further comprising moving the second carriage along the arcuate path with a prime mover coupled to the drive link.

14. The method of claim 13, further comprising selecting an automated mode of the device in which at least one degree of freedom is driven by a computer controlled actuator.

15. The method of claim 10, further comprising manually moving the end effector, and allowing the drive link to follow the motion of the second carriage and constrain the second carriage to move along the arcuate path.

16. The method of claim 15, further comprising selecting a powered assist mode of the device in which manual movements of the end effector are sensed and a prime mover provides force to assist with those movements.

17. The method of claim 16, further comprising alternately selecting between the manual mode, the powered assist mode, and an automated mode of the device in which at least one degree of freedom is driven by a computer controlled actuator.

18. The method of claim 10, further comprising providing an intravenous line inserter on the end effector.

* * * * *